(12) United States Patent
Giudiceandrea

(10) Patent No.: US 8,408,081 B2
(45) Date of Patent: Apr. 2, 2013

(54) METHOD AND APPARATUS FOR DETERMINING THE NODOSITY OF A WOODEN PLANK

(75) Inventor: Federico Giudiceandrea, Bressanone (IT)

(73) Assignee: Microtec S.R.L., Bressanone (IT)

( * ) Notice: Subject to any disclaimer, the term of this patent is extended or adjusted under 35 U.S.C. 154(b) by 421 days.

(21) Appl. No.: 12/877,708

(22) Filed: Sep. 8, 2010

(65) Prior Publication Data
US 2011/0061479 A1    Mar. 17, 2011

(30) Foreign Application Priority Data
Sep. 11, 2009 (EP) ...................................... 09425349

(51) Int. Cl.
| | |
|---|---|
| *G01N 33/46* | (2006.01) |
| *G01N 21/88* | (2006.01) |
| *G01N 21/89* | (2006.01) |
| *G01F 17/00* | (2006.01) |

(52) U.S. Cl. ........... 73/866; 73/149; 356/237.2; 702/35; 702/81; 702/156

(58) Field of Classification Search ............... 73/149, 73/865.8, 866; 356/237.2, 237.5, 402, 627, 356/939, FOR. 100, FOR. 134; 702/35, 81, 702/83, 156, FOR. 125, FOR. 149
See application file for complete search history.

(56) References Cited

U.S. PATENT DOCUMENTS

| | | | | |
|---|---|---|---|---|
| 4,255,024 A | * | 3/1981 | de Monts et al. ................ | 351/41 |
| 4,916,629 A | * | 4/1990 | Bogue et al. ..................... | 702/40 |
| 4,941,357 A | * | 7/1990 | Schajer ........................... | 73/600 |
| 5,023,805 A |   | 6/1991 | Aune et al. |   |
| 5,335,790 A | * | 8/1994 | Geiger et al. .................. | 209/518 |
| 5,394,342 A | * | 2/1995 | Poon .............................. | 702/137 |
| 5,585,732 A | * | 12/1996 | Steele et al. ................... | 324/663 |
| 5,820,180 A | * | 10/1998 | Haupt ............................. | 294/16 |
| 6,157,698 A |   | 12/2000 | Pietikainen et al. |   |

(Continued)

FOREIGN PATENT DOCUMENTS

| | | |
|---|---|---|
| GB | 1 489 554 A | 10/1977 |
| WO | 97/32199 A1 | 9/1997 |

OTHER PUBLICATIONS

Adjanohoun G. et al., "Small Roundwood Grading by Non-Destructive X-Rays and Ultrasonic Waves Methods", 5th World Conference on Timber Engineering, vol. 4, No. 11, Aug. 17, 1998-Aug. 20, 1998, 4 pages, XP002566994.

*Primary Examiner* — Thomas P Noland
(74) *Attorney, Agent, or Firm* — Pearne & Gordon LLP

(57) ABSTRACT

A method for determining the nodosity of a wooden plank comprises the operating steps of observing the lateral surface (4) of the wooden plank (1) to identify its zones (7) corresponding to knots (6), assessing the overall extent of the knots (6) inside the plank (1) and the relative volume, and determining the nodosity as a ratio of the volume occupied by the knots (6) to the overall volume of the plank (1) or the remaining volume of the plank (1). The step of assessing the extent of the knots (6) in turn comprises the operating steps of estimating the position in space, relative to the plank (1), of the longitudinal axis (8) of the log (2) from which the plank (1) was obtained and assuming that each knot (6) comprises a conical body extending radially from the longitudinal axis (8) with the vertex on the longitudinal axis, and passing through the zone (7) of the lateral surface (4) of the plank (1) corresponding to the knot (6), and calculating the volume of the knots (6) as the intersection between said bodies and the plank (1).

18 Claims, 4 Drawing Sheets

U.S. PATENT DOCUMENTS

| | | |
|---|---|---|
| 6,757,354 B2 * | 6/2004 | Skatter et al. .................. 378/58 |
| 6,784,672 B2 * | 8/2004 | Steele et al. .................. 324/663 |
| 8,253,793 B2 * | 8/2012 | Hiraoka .......................... 348/92 |
| 2004/0057551 A1 * | 3/2004 | Skatter et al. .................. 378/54 |
| 2005/0031158 A1 | 2/2005 | Biernacki et al. |
| 2005/0190958 A1 | 9/2005 | Woods et al. |
| 2008/0237096 A1 * | 10/2008 | Huang .......................... 209/517 |
| 2008/0246971 A1 | 10/2008 | Huang et al. |

* cited by examiner

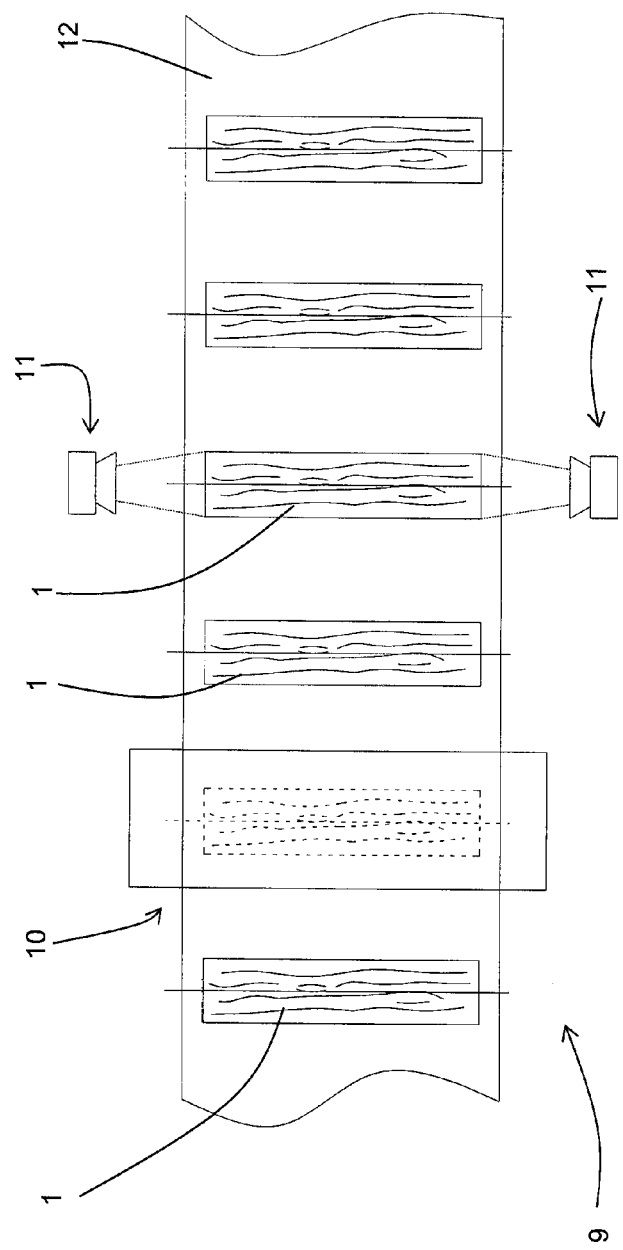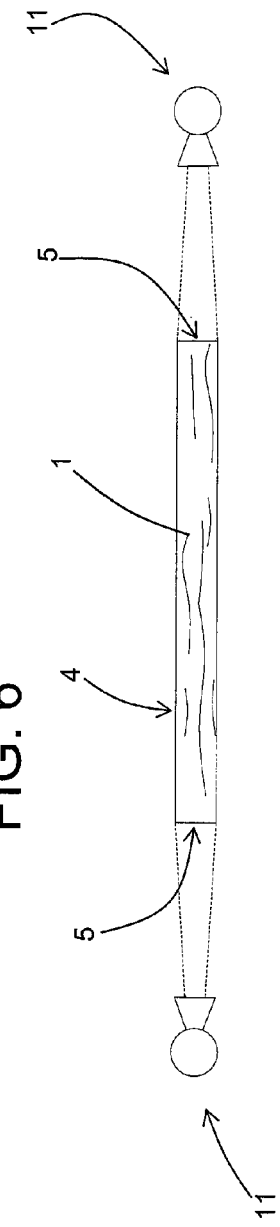

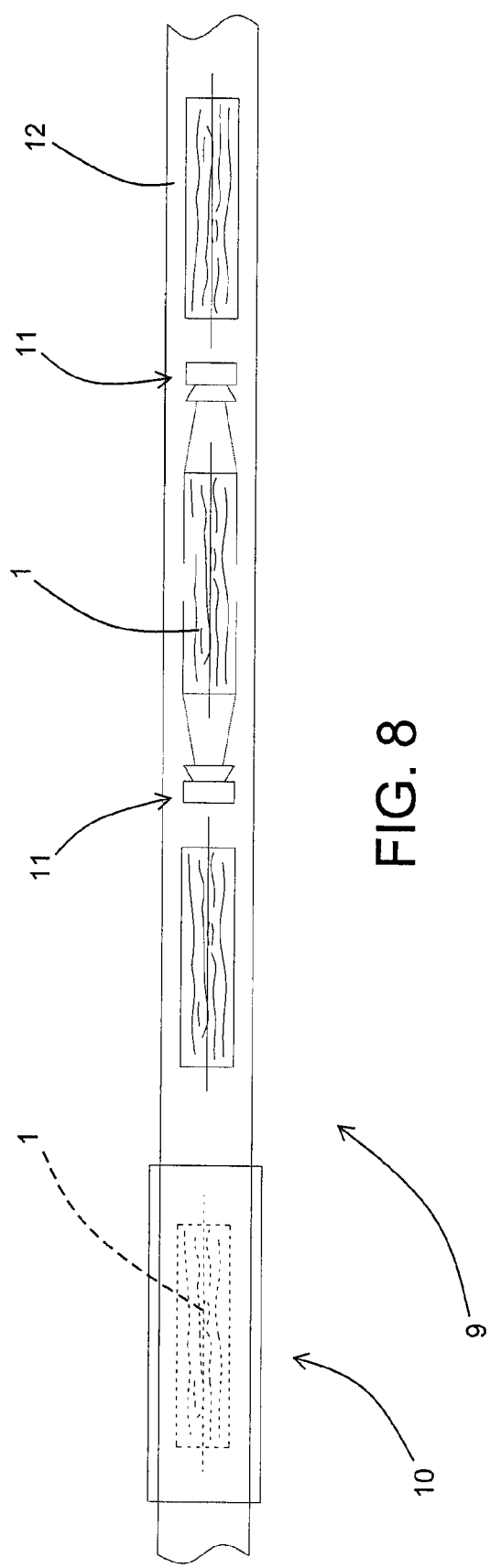
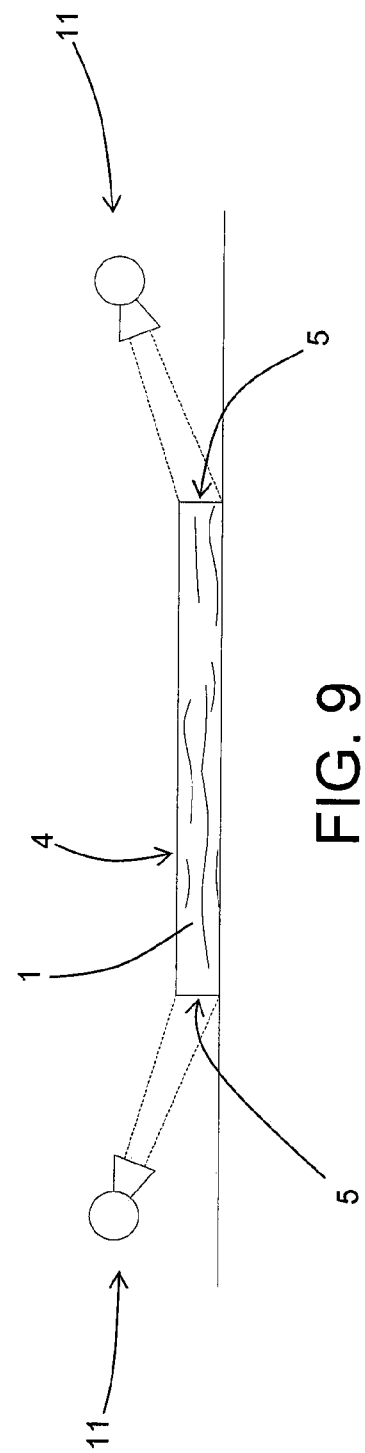
FIG. 8
FIG. 9

METHOD AND APPARATUS FOR DETERMINING THE NODOSITY OF A WOODEN PLANK

This invention relates to a method and an apparatus for determining the nodosity of a wooden plank.

The term nodosity refers to the ratio of the volume of wood where knots are present to the overall volume of the plank or the volume of wood where there are no knots present, it being possible to select either of the latter two.

Nodosity is a fundamental parameter for assessing the mechanical properties of wooden planks, since such planks are better the more wood fibers are angled in the main direction of extension of the planks. In contrast, at knots, the wood fibers are angled perpendicular to the main direction of extension of the plank, and therefore the mechanical properties are poor.

The first prior art method for estimating nodosity is based exclusively on the experience of an operator who, observing the arrangement and size of the knots present on the outer surface of the plank, must be able to assign the nodosity range to that plank.

However, that operating method proved unusable in modern wood processing plants where high productivity is required.

Consequently, over the years various solutions were studied for the automated inspection of nodosity. The solution most widely applied is based on the combination of the outer appearance of the planks and an X-ray examination of them.

In particular, the apparatus intended to assess the nodosity can on one hand detect the outer appearance of the planks and, using known image processing algorithms, determine the zones of the surface corresponding to knots (typically characterised by a different color), and on the other hand take one or more X-rays of the planks to obtain the projection in a plane of the extent of the various knots. Special processing algorithms then combine the various data to reconstruct to a first approximation the trend of the knots inside the plank and the relative volume.

However, this prior art technology also has several disadvantages.

First, it is a relatively expensive technology since it requires the use of an X-ray machine.

Second, the results obtainable are only reliable for planks with few knots which are not superposed in the X-rays. Otherwise, if there are many knots present, which are superposed in the X-rays, the precise reconstruction of each of them is practically impossible.

In addition, to avoid a negative impact on plant productivity, the X-ray machine must be positioned along the plank movement path, significantly increasing the dimensions and length of the movement lines.

Moreover, both of the techniques described are not very reliable when the surface of the plank has many knots on different faces. In such cases, the prior art techniques do not allow one to establish whether or not two knots visible on two different faces are in reality the same knot or two separate knots, nor whether or not said knots originate inside the plank.

Moreover, with the prior art techniques it is quite probable that the same knot will be considered twice or that two separate knots will be considered as a single knot.

In this situation, the technical purpose which forms the basis of this invention is to provide a method and an apparatus for determining the nodosity of a wooden plank which overcomes the above-mentioned disadvantages.

In particular, the technical purpose of this invention is to provide a method and an apparatus for determining the nodosity of a wooden plank which is relatively simple and guarantees good reliability for the results obtainable.

This invention also has for a technical purpose to provide a compact apparatus for determining the nodosity of a wooden plank.

The technical purpose specified and the aims indicated are substantially achieved by a method and an apparatus for determining the nodosity of a wooden plank as described in the appended claims.

Further features and the advantages of this invention are more apparent in the detailed description of several preferred, non-limiting embodiments of a method and an apparatus for determining the nodosity of a wooden plank, with reference to the accompanying drawings, in which:

FIG. 6 is a top view of a first apparatus made according to the present invention;

FIG. 7 is a longitudinal view of a detail of the apparatus of FIG. 6;

FIG. 8 is a top view of a second apparatus made according to the present invention; and FIG. 9 is a lateral view of a detail of the apparatus of FIG. 8.

Figure 1:
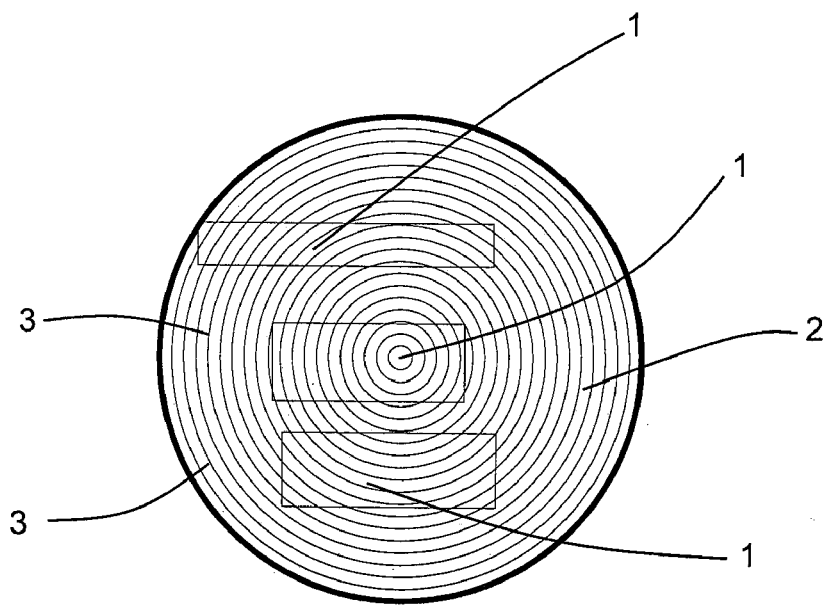
FIG. 1 is a front view of the end of a log showing three planks which can be obtained from it.

For the reasons of mechanical strength indicated at the start of this text, wooden planks 1 are usually cut from a log 2 in such a way that their main direction of extension is substantially parallel with the main direction of extension of the log 2. Said situation is illustrated in FIG. 1, which shows a cross-section of the end of a log 2 (indicating the growth rings 3 for reasons which will become clearer below) and the positions of three example planks 1 which may be obtained, having different shapes and dimensions. In each case, each plank has a lateral surface 4 (which in turn comprises a plurality of faces—four in the embodiments illustrated) substantially parallel with its main direction of extension (into the drawing) and two end surfaces 5 substantially transversal to the main direction of extension (in the case illustrated the end surfaces 5 are perpendicular to the main direction of extension).

Figure 3:
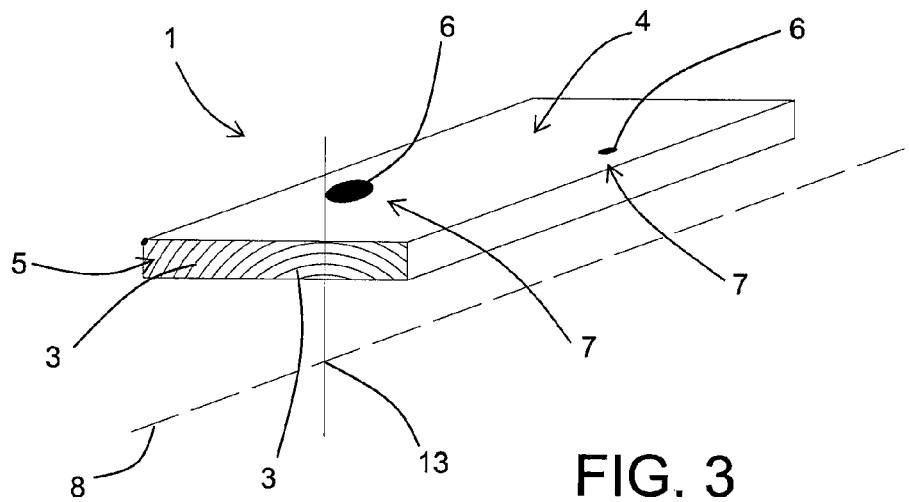
FIG. 3 is an axonometric view of the upper plank amongst those illustrated in FIG. 1, showing the knots present in it and the position of the longitudinal axis of the log relative to the plank.
Figure 4:
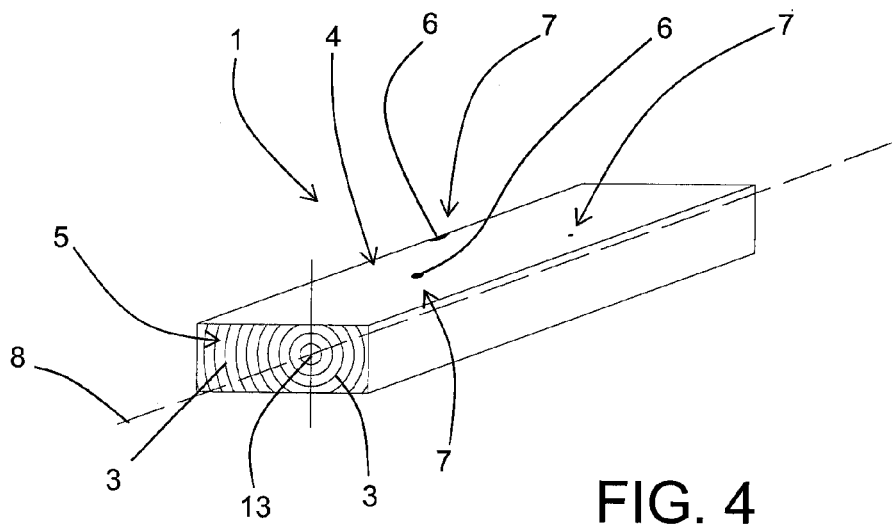
FIG. 4 is an axonometric view of the central plank amongst those illustrated in FIG. 1, showing the knots present in it and the position of the longitudinal axis of the log relative to the plank.
Figure 5:
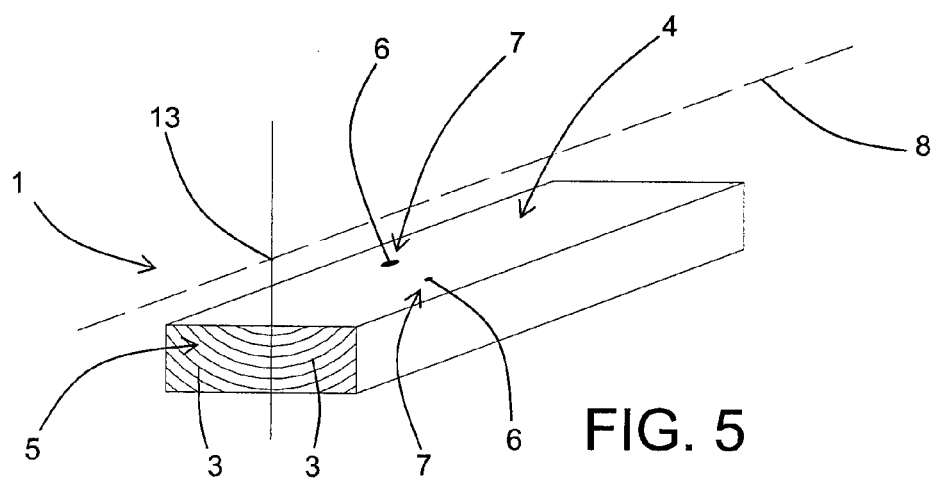
FIG. 5 is an axonometric view of the lower plank amongst those illustrated in FIG. 1, showing the knots present in it and the position of the longitudinal axis of the log relative to the plank.

The three planks 1 are shown in axonometric views in FIGS. 3 to 5. On the lateral surface 4 of each plank black marks are used to indicate several knots 6 present in them.

Figure 2:
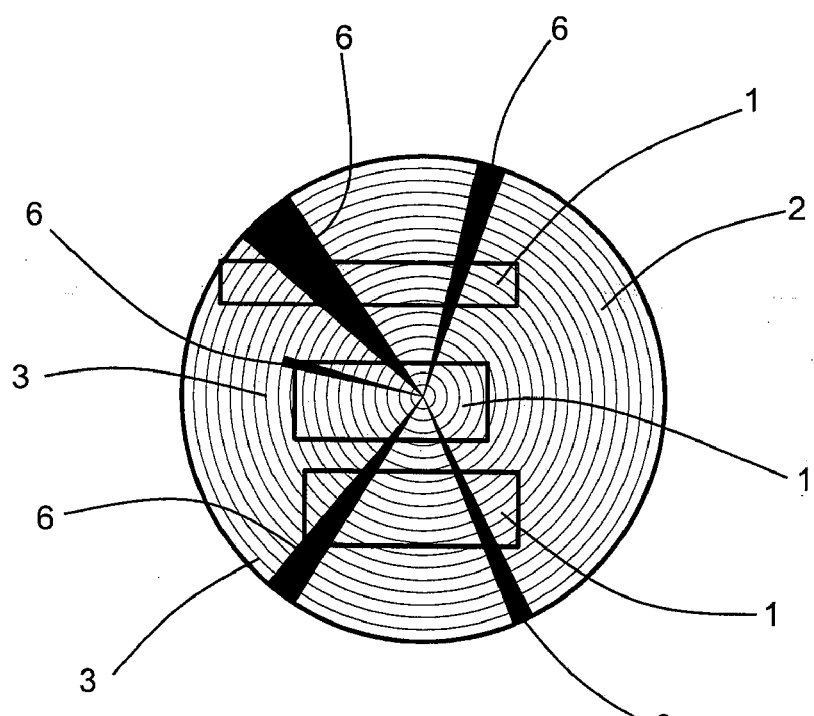
FIG. 2 is a schematic projection on the end of the log of FIG. 1, of the knots present along the log.

Although the knots 6 lie at different cross-sections along the main direction of extension of the planks 1, for simple reference, FIG. 2 shows their projection on the front face of the log 2 illustrated in FIG. 1.

The method for determining the nodosity of a wooden plank 1 according to this invention in general comprises first an operating step in which the lateral surface 4 of the wooden plank 1 is observed to identify its zones 7 corresponding to knots 6. In other words, it involves identifying those zones 7 which, in FIGS. 3 to 5 are indicated with black marks.

As already indicated, observing and inspecting the outer surface of the planks 1 to identify the zones 7 corresponding to knots 6 may be done easily using known image processing algorithms, which are therefore not described in detail herein.

The second step of the method according to this invention involves assessing the overall extent of the knots 6 inside the plank 1 and the relative volume. Finally, the last step involves determining the nodosity as a ratio of the volume occupied by the knots 6 to the overall volume of the plank 1 or the volume of the plank 1 which is free of knots 6.

The innovative aspect of this invention is the way in which the step of assessing the extent of the knots 6 is carried out.

It is divided into a plurality of operating steps.

First, there is an inspection of at least one end surface 5 of the plank 1 to detect at this end surface the development curves of the growth rings 3 belonging to the log 2 from which the wooden plank 1 was obtained.

Said curves are schematically illustrated in each of the FIGS. from 1 to 5 and can be detected by detecting an image of the end surface 5 and processing the image with suitable algorithms based on the change of color in the wood at each ring 3. In any case, the algorithms again being known to experts in the field, they are not described in detail herein.

Moreover, as illustrated in more detail below with reference to the description of the apparatus, the image of the end surface 5 of the planks 1 can advantageously be acquired during plank 1. movement along a feed path.

Once the development curves of the growth rings 3 have been detected, the method according to this invention involves the operating step of estimating the position in space, relative to the plank 1, of the longitudinal axis 8 of the log 2 from which the plank 1 was previously obtained. In particular, said estimate is made based on the trend of the development curves of the growth rings 3.

According to the most simple method of implementation, the step of estimating the position of the longitudinal axis 8 of the log 2 involves first approximating the development curve of at least one of the rings 3 with a circle or an ellipse. Although in nature no curve can have a perfect geometrical shape, this approximation allows, in general, an approximation of the effective trend of the ring 3 with excellent precision.

Once the circle or the ellipse which best approximates the development curve of the ring 3 has been found, it is possible to identify the point of intersection 13 between the longitudinal axis 8 of the log 2 and the plane in which the end surface 5 lies, as the centre of said circle or ellipse. All of the rings 3 grow concentrically, being substantially centered on the longitudinal axis 8 of the log 2.

At that point, it may be assumed that the longitudinal axis 8 of the log 2 is a straight line parallel with the main direction of extension of the plank 1 and passing through the point of intersection 13 (that is to say, through the centre of the circle or the ellipse).

To minimize the error caused by possible irregularities in the development of a particular ring 3, the step of approximating the development curve may be repeated for a plurality of rings 3 identified on the end surface 5, and the point of intersection 13 may be identified as the weighted average of the positions of the centres of the circles or the ellipses obtained. In particular, the term weighted average refers to an average found with statistical techniques (for example, based on standard deviation, or another aspect) so as to exclude any values which are obviously the result of an anomaly in a growth ring 3.

However, in the preferred embodiments of the invention the step of inspecting at least one end surface 5 just described is repeated for both of the end surfaces 5 of the plank 1, and the step of estimating the position in space, relative to the plank 1, of the longitudinal axis 8 of the log 2 from which the plank 1 was obtained, is carried out based on the trend of the development curves of the rings 3 on both of the end surfaces 5. In particular, for each end surface 5 the point of intersection 13 between the longitudinal axis 8 of the log 2 and the plane in which the end surface 5 lies is detected according to one of the methods indicated above.

At that point it is assumed that the longitudinal axis 8 is a straight line passing through the two points of intersection thus identified.

The advantage of this operating method is that it allows an improved approximation even of logs in which the longitudinal axis 8 is curved rather than straight.

Once the position relative to the plank 1 of the longitudinal axis 8 of the log 2 has been identified according to the above-mentioned methods, the method according to this invention involves assuming that each knot 6 identified on the outer surface extends, in the log 2 from which the plank 1 was cut, as a conical body extending radially from the longitudinal axis 8, with its vertex on the longitudinal axis, and passing through the zone 7 of the lateral surface 4 of the plank 1 corresponding to the knot 6. In other words, said zone 7 represents the cross-section of the conical body in the plane in which the lateral surface 4 lies. That schematization of the knots 6 is shown in FIG. 2.

However, it should be noticed that the term conical body refers not to a conventional cone according to classic geometrical definitions, but to a solid consisting of the combination of all of the straight lines extending from the vertex and passing through all of the points of the zone 7 of the surface corresponding to the knot 6.

Advantageously, the vertex of each conical body representing a knot 6 is assumed to be at the point of intersection between the longitudinal axis 8 of the log 2 and a straight line substantially perpendicular to it passing through a substantially central point of the zone 7 of the outer surface corresponding to the knot 6. According to the embodiments, said central point may be the centre of gravity of the zone 7, the centre of the maximum circle inscribable in it, that of the circle circumscribable around the zone 7, etc.

At this point, the method involves calculating the volume of the knots 6 as the volume of the intersection between the conical bodies and the plank 1.

The apparatus 9 for determining nodosity according to this invention comprises first detection means 10 for detecting the appearance of the lateral surface 4 of the planks 1, and second detection means 11 for detecting the appearance of at least one end surface 5 of the planks 1. The first detection means 10 and the second detection means 11 (which may be combined in one) are operatively connected to a processing unit (not illustrated) which receives the imagines they detect and which is programmed to implement the method described above.

Two examples of an apparatus 9 according to this invention are illustrated in FIGS. 6 to 9. In both cases there are feed means 12 for feeding the planks 1 along a movement path, and the first and second detection means 10, 11 are positioned along the movement path in such a way that they can detect the images of the lateral surfaces 4 and the end surfaces 5 of the planks 1 as they are fed.

In particular, in the case in FIGS. 6 and 7, the feed means 12 are designed to feed the planks 1 perpendicularly to their main direction of extension. In this case, the second detection means 11 comprise one or two detectors (two in the accompanying drawings) positioned at the sides of the feed path and substantially aligned with the axis of the planks 1 at the moment of detection (FIG. 7).

In contrast, in the case in FIGS. 8 and 9, the feed means 12 are designed to feed the planks 1 parallel with their main direction of extension. In this case, the second detection means 11 comprise one or two detectors (two in the accompanying drawings) positioned in such a way that they are aligned with the feed path and substantially above it and angled downwards (FIG. 9) so that they can detect the images of the end surfaces 5 at the moment when the planks 1 pass below them. Obviously, in other embodiments the second detection means may be positioned below the movement path.

This invention brings important advantages.

First, thanks to this invention it is possible to determine the nodosity of planks with excellent precision and with a relatively limited cost.

Second, thanks to this invention it is also possible to minimize dimensions along processing lines.

It should also be noticed that this invention is relatively easy to produce.

The invention described above may be modified and adapted in several ways without thereby departing from the scope of the inventive concept.

Moreover, all details of the invention may be substituted with other technical equivalent elements and in practice all of the materials used, as well as the shapes and dimensions of the various components, may vary according to requirements.

The invention claimed is:

1. A method for determining the nodosity of a wooden plank having a main direction of extension, a lateral surface (4) substantially parallel with the main direction of extension and two end surfaces (5) substantially transversal to the main direction of extension, comprising the operating steps of:
    observing the lateral surface (4) of the wooden plank (1) to identify its zones (7) corresponding to knots (6);
    assessing the overall extent of the knots (6) inside the plank (1) and the relative volume; and
    determining the nodosity as a ratio of the volume occupied by the knots (6) to the overall volume of the plank (1) or the remaining volume of the plank (1);
    the method being characterised in that the step of assessing the extent of the knots (6) in turn comprises the operating steps of:
    inspecting at least one end surface (5) of the plank (1) to detect at this end surface the development curves of the growth rings (3) belonging to the log (2) from which the wooden plank (1) was obtained;
    based on the trend of the development curves of the rings (3), estimating the position in space, relative to the plank (1), of the longitudinal axis (8) of the log (2) from which the plank (1) was obtained;
    assuming that each knot (6) identified on the outer surface extends, inside the log (2) from which the plank (1) was cut, as a conical body extending radially from the longitudinal axis (8) with its vertex on the longitudinal axis, and passing through the zone (7) of the lateral surface (4) of the plank (1) corresponding to the knot (6); and
    calculating the volume of the knots (6) as the intersection between said bodies and the plank (1).

2. The method according to claim 1, characterised in that the step of estimating the position of the longitudinal axis (8) of the log (2) involves the operating steps of:
    approximating the development curve of at least one of the rings (3) with a circle or an ellipse;
    identifying the point of intersection (13) between the longitudinal axis (8) of the log (2) and the plane in which the end surface (5) lies, as the centre of said circle or ellipse; and
    assuming that the longitudinal axis (8) is a straight line parallel with the main direction of extension of the plank (1) and passing through the point of intersection (13).

3. The method according to claim 2, characterised in that the step of approximating the development curve is repeated for a plurality of the rings (3), and also being characterised in that the point of intersection (13) is identified as the weighted average of the positions of the centres of the circles or ellipses which approximate the development curves of the rings (3).

4. The method according to claim 3, characterised in that the vertex of each conical body representing a knot (6) is assumed to be at the point of intersection between the longitudinal axis (8) of the log (2) and a straight line substantially perpendicular to it passing through a substantially central point of the zone (7) of the outer surface corresponding to the knot (6).

5. The method according to claim 2, characterised in that the vertex of each conical body representing a knot (6) is assumed to be at the point of intersection between the longitudinal axis (8) of the log (2) and a straight line substantially perpendicular to it passing through a substantially central point of the zone (7) of the outer surface corresponding to the knot (6).

6. The method according to claim 1, characterised in that the step of inspecting at least one end surface (5) of the plank (1) involves inspecting both of the end surfaces (5) of the plank (1) to detect at each of them the development curves of the log (2) growth rings (3), and also being characterised in that the step of estimating the position in space relative to the plank (1) of the longitudinal axis (8) of the log (2) from which the plank (1) was obtained is carried out based on the trend of the development curves of the rings (3) on both of the end surfaces (5).

7. The method according to claim 6, characterised in that the step of estimating the position of the longitudinal axis (8) of the log (2) involves, for each of the end surfaces (5), the operating steps of:
    approximating the development curve of at least one of the rings (3) with a circle or an ellipse; and
    identifying the point of intersection (13) between the longitudinal axis (8) of the log (2) and the plane in which the respective end surface (5) lies, as the centre of said circle or ellipse;
    and the operating step of assuming that the longitudinal axis (8) is a straight line passing through the two points of intersection thus identified.

8. The method according to claim 7, characterised in that the step of approximating the development curve is repeated for a plurality of the rings (3), and also being characterised in that for each end surface (5), the point of intersection (13) is identified as the weighted average of the positions of the centres of the circles or ellipses which approximate the development curves of the rings (3).

9. The method according to claim 8, characterised in that the vertex of each conical body representing a knot (6) is assumed to be at the point of intersection between the longitudinal axis (8) of the log (2) and a straight line substantially perpendicular to it passing through a substantially central point of the zone (7) of the outer surface corresponding to the knot (6).

10. The method according to claim 7, characterised in that the vertex of each conical body representing a knot (6) is assumed to be at the point of intersection between the longitudinal axis (8) of the log (2) and a straight line substantially perpendicular to it passing through a substantially central point of the zone (7) of the outer surface corresponding to the knot (6).

11. The method according to claim 6, characterised in that the vertex of each conical body representing a knot (6) is assumed to be at the point of intersection between the longitudinal axis (8) of the log (2) and a straight line substantially perpendicular to it passing through a substantially central point of the zone (7) of the outer surface corresponding to the knot (6).

12. The method according to claim 6, characterised in that the step of inspecting at least one end surface (5) of the plank (1) involves detecting an image of the end surface (5) as the plank (1) is moved along a feed path.

13. An apparatus for determining the nodosity of wooden planks having a main direction of extension, a lateral surface (4) substantially parallel with the main direction of extension and two end surfaces (5) substantially transversal to the main direction of extension, comprising:
  first detection means (10) for detecting the appearance of the lateral surface (4) of the planks (1);
  second detection means (11) for detecting the appearance of at least one end surface (5) of the planks (1);
  a processing unit operatively connected to the first detection means (10) and to the second detection means (11) and programmed to implement the method according to claim 6.

14. The apparatus according to claim 13, characterised in that it also comprises feed means (12) for feeding the planks (1) along a movement path, the first detection means and the second detection means (11) being positioned along the movement path.

15. The method according to claim 1, characterised in that the vertex of each conical body representing a knot (6) is assumed to be at the point of intersection between the longitudinal axis (8) of the log (2) and a straight line substantially perpendicular to it passing through a substantially central point of the zone (7) of the outer surface corresponding to the knot (6).

16. The method according to claim 1, characterised in that the step of inspecting at least one end surface (5) of the plank (1) involves detecting an image of the end surface (5) as the plank (1) is moved along a feed path.

17. An apparatus for determining the nodosity of wooden planks having a main direction of extension, a lateral surface (4) substantially parallel with the main direction of extension and two end surfaces (5) substantially transversal to the main direction of extension, comprising:
  first detection means (10) for detecting the appearance of the lateral surface (4) of the planks (1);
  second detection means (11) for detecting the appearance of at least one end surface (5) of the planks (1);
  a processing unit operatively connected to the first detection means (10) and to the second detection means (11) and programmed to implement the method according to claim 1.

18. The apparatus according to claim 17, characterised in that it also comprises feed means (12) for feeding the planks (1) along a movement path, the first detection means and the second detection means (11) being positioned along the movement path.

* * * * *